US012609484B2

(12) United States Patent
Shire et al.

(10) Patent No.:     US 12,609,484 B2
(45) Date of Patent:        Apr. 21, 2026

(54) IMPLANTABLE IN-LINE HIGH DENSITY CONNECTOR

(71) Applicants: Case Western Reserve University, Cleveland, OH (US); The United States as represented by the Department of Veterans Affairs, Cleveland, OH (US)

(72) Inventors: Douglas Bourne Shire, Cleveland, OH (US); Dustin J. Tyler, Cleveland, OH (US); Janet L. Gbur, Cleveland, OH (US)

(73) Assignees: Case Western Reserve University, Cleveland, OH (US); The United States as represented by the Department of Veterans Affairs, Washington, DC (US)

( * ) Notice: Subject to any disclaimer, the term of this patent is extended or adjusted under 35 U.S.C. 154(b) by 467 days.

(21) Appl. No.: 18/015,357

(22) PCT Filed: Jul. 15, 2021

(86) PCT No.: PCT/US2021/041839
    § 371 (c)(1),
    (2) Date: Jan. 10, 2023

(87) PCT Pub. No.: WO2022/015990
    PCT Pub. Date: Jan. 20, 2022

(65) Prior Publication Data
    US 2023/0291143 A1     Sep. 14, 2023

Related U.S. Application Data

(60) Provisional application No. 63/051,920, filed on Jul. 15, 2020.

(51) Int. Cl.
    *A61N 1/37*     (2006.01)
    *A61N 1/375*     (2006.01)
    (Continued)

(52) U.S. Cl.
    CPC ........... *H01R 13/621* (2013.01); *A61N 1/375* (2013.01); *H01R 24/58* (2013.01); *H01R 2201/12* (2013.01)

(58) Field of Classification Search
    CPC ...... A61N 1/375; H01R 24/62; H01R 13/621; H01R 24/58; H01R 2201/12
    See application file for complete search history.

(56) References Cited

U.S. PATENT DOCUMENTS 4,466,441 A     8/1984  Skubitz et al.
6,327,502 B1 *  12/2001  Johansson .......... A61N 1/37512
                                                    607/36
(Continued)

FOREIGN PATENT DOCUMENTS

WO          2018156953 A1     8/2018

OTHER PUBLICATIONS

Extended European search report dated Jun. 27, 2024 for corresponding application/Patent No. 21843249.0-1122 /4182007 PCT/US2021041839, 7 pages.
(Continued)

*Primary Examiner* — Eric D. Bertram
(74) *Attorney, Agent, or Firm* — Tarolli, Sundheim, Covell & Tummino LLP

(57)          ABSTRACT
An inline implantable connector device can provide an increased volume density to medical device systems in a limited volume. The inline implantable connector device can have a claim-shell design with a first half and a second half, each having a conductive path in a same design. The second half is turned and flipped by 180 degrees to mate with the
(Continued)

first half so that the conductive paths interconnect to form electrical and mechanical interconnections that are fundamentally transverse to the direction of the incoming or outgoing lead wires. A first screw hole on a top side of the connector device can accept a screw therethrough; and a second screw hole on a bottom side of the connector device can accept another screw therethrough.

21 Claims, 9 Drawing Sheets

(51) Int. Cl.
    *H01R 13/621*     (2006.01)
    *H01R 24/58*     (2011.01)

(56)           References Cited

U.S. PATENT DOCUMENTS

| | | | | |
|---|---|---|---|---|
| 7,534,127 | B2 * | 5/2009 | Parker ................ | A61N 1/3752 |
| | | | | 439/425 |
| 7,794,256 | B1 * | 9/2010 | Sochor ............... | H01R 13/025 |
| | | | | 439/289 |
| 8,140,163 | B1 * | 3/2012 | Daglow .............. | H01R 13/193 |
| | | | | 607/36 |
| 8,251,731 | B2 | 8/2012 | Boyd et al. | |
| 8,515,555 | B1 * | 8/2013 | Jones ................. | A61N 1/3605 |
| | | | | 607/115 |
| 10,218,111 | B2 * | 2/2019 | Schüttler .............. | A61N 1/375 |
| 2010/0331924 | A1 * | 12/2010 | North ................. | A61N 1/3754 |
| | | | | 439/660 |
| 2011/0015686 | A1 * | 1/2011 | Kara .................... | A61N 1/375 |
| | | | | 427/2.24 |
| 2011/0065301 | A1 * | 3/2011 | Boyd ............... | H01R 13/5224 |
| | | | | 439/271 |
| 2017/0237199 | A1 * | 8/2017 | Schüttler .......... | H01R 13/5224 |
| | | | | 439/277 |

OTHER PUBLICATIONS

Australian Government IP Australia Examination Report No. 1 dated Nov. 28, 2023 for corresponding application No. 2021308626; Applicants: Case Western Reserve University, The United States as Represented by the Department of Veterans Affairs, pp. 1-4.
PCT Search Report and Written Opinion for corresponding Application Serial No. PCT/US 21/41839 with a date of issuance of report of Jan. 17, 2023, pp. 1-6.
PCT International Search Report for corresponding International Application Serial No. PCT/US2021/041839, mailed Nov. 15, 2021, 1 page.

* cited by examiner

SECTION A-A
SCALE 3:1

SECTION B-B
SCALE 3:1

42

44

52b

32b

DETAIL C
SCALE 12 : 1

SOLDERED, CRIMPED
CONTACT WIRE

72

74b

44

110

112

IMPLANT A MEDICAL DEVICE SYSTEM IN A PATIENT'S BODY WITH AN INLINE INPLANTABLE CONNECTOR DEVICE

114

DETECT A NEED TO MAINTAIN OR REPLACE AN ELECTRONIC MODULE IN A MEDICAL DEVICE SYSTEM

116

DISCONNECT THE ELECTRONIC MODULE FROM THE INLINE INPLANTABLE CONNECTOR DEVICE TO MAINTAIN OR REPLACE THE ELECTRONIC MODULE

120

122
PRINT TWO EQUIVALENT CIRCUITS WITH CONDUCTIVE PADS AND PATHWAYS ON A SUBSTRATE

124
CONNECT AT LEAST ONE LEAD WIRE TO A PAD OF EACH EQUIVALENT CIRCUIT

126
TURN AND FLIP ONE OF THE TWO EQUIVALENT CIRCUITS

128          PRESS EQUIVALENT CIRCUITS TOGETHER

130          CLOSE DEVICE

IMPLANTABLE IN-LINE HIGH DENSITY CONNECTOR

CROSS-REFERENCE TO RELATED APPLICATION

This application claims the benefit of U.S. Provisional Application Ser. No. 63/051,920, filed Jul. 15, 2020, entitled "IMPLANTABLE IN-LINE HIGH DENSITY 32-CHANNEL CONNECTOR", the entirety of which is hereby incorporated by reference for all purposes.

GOVERNMENT SUPPORT

This invention was made with government support under 101RX002789 and 121RX001361 awarded by VA Rehabilitation R&D. The government has certain rights in the invention.

TECHNICAL FIELD

This disclosure generally relates to implantable medical device systems and, more specifically, to an implantable in-line high density connector with increased volume density that can be utilized by implantable medical device systems.

BACKGROUND

Generally, implantable medical device systems, such as neuromodulation systems, cardiac pacemakers, or the like, can include leads that are implanted in the body. Inline connectors ensure that one portion of the implantable medical device system (e.g., an electronics module) can be replaced or upgraded without having to disturb the rest of the implantable medical device system (e.g., electrodes, actuators, sensors, etc.). The rest of the implantable medical device system can be left in place without having to remove or replace the entire medical device system. In so doing, the implantable medical device system as a whole becomes more reparable and safer.

However, presently-available inline connectors tend to be rather bulky compared to the overall implantable medical devices systems of which they are a part, occupying valuable physical space or volume within the body. In fact, it is now possible for an electronics module for implantation in the body to be smaller than the volume of the inline connectors to which the electronics module is attached. Presently-available inline connectors have a "male" connector portion and a "female" connector portion made up of a multi-contact plug and socket. Electrical interconnections are facilitated by coiled springs in the socket that contact a mating rod of the plug (with each channel requiring its own coiled spring assembly). Silicone barriers separate the individual channels. Since each additional channel adds to the total volume needed to form all of the interconnections, there is a need to reduce the overall volume of implantable inline connectors, while at the same time also expanding the number of interconnections that can be formed at the same time with one implantable inline connector unit.

SUMMARY

The present disclosure provides an implantable in-line high density connector with increased volume density that can be utilized by implantable medical device systems.

In an aspect, an inline implantable connector for a medical device system in with a limited volume and high density is described. The inline implantable connector device can have a claim-shell design with a first half and a second half, each having a conductive path in a same design. The second half is turned around by 180 degrees to mate with the first half so that the conductive paths interconnect to form electrical and mechanical interconnections that are fundamentally transverse to the direction of the incoming or outgoing lead wires. A first screw hole on a top side of the connector device can accept a screw therethrough; and a second screw hole on a bottom side of the connector device can accept another screw therethrough.

In another aspect, methods for using and constructing the implantable inline high density connector device to allow a module to be disconnected without affecting the entire medical device system. Advantageously, the implantable connector device has an increased volume density while occupying a smaller space than previously-available inline connectors. The implantable inline high density connector eliminates empty space and air pockets within the implantable inline high density connector device.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figures 1, 2:
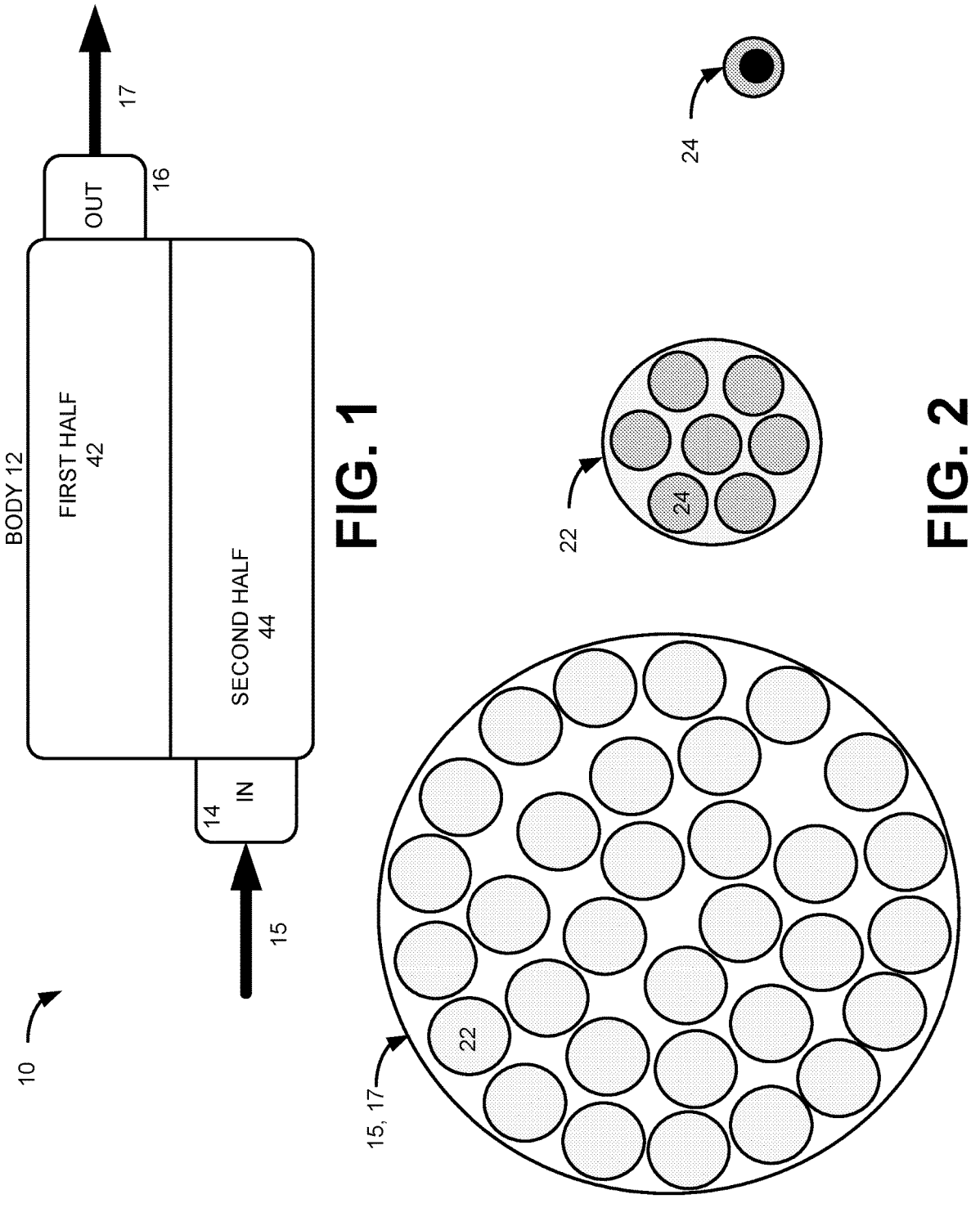
FIG. 1 is a block diagram showing an implantable inline high density connector.
FIG. 2 is an illustration of an example hierarchy.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "medical device system" can refer to a combination of products intended to be interconnected or combined to achieve a specific medical purpose. Medical device systems can be at least partially implantable. Examples of medical device systems can include neural modulation systems, cardiac pacemakers, etc.

As used herein, the term "implantable" can refer to something that is capable of being or designed to be inserted or fixed within a living body.

As used herein, the terms "inline connector" or "in-line connector" can be used interchangeably to refer to something that interconnects two or more components of a medical device system together and maintains signal continuity between the two or more components. An inline connector can be implantable, for example as part of the medical device system. In some instances, the inline connector can have a high density with a relatively small size (smaller than those currently for sale).

As used herein, the term "high density" can refer to something having a large capacity or concentration.

As used herein, a "lead" can be an input to or an output from an inline connector. A lead can include a grouping of a large number of channels (e.g., 8, 16, 32, 64, etc.), each within an insulating casing. A "wire lead" can refer to a lead traveling within the inline connector.

As used herein, the term "channel" or "strand" can refer to a group of wires defined by an insulating casing. For example, seven wires can be within a channel and a large number of channels can be within a lead (e.g., 8, 16, 32, 64, etc.).

As used herein, the terms "wire" can refer to a physical carrier of electric current. The wire can be constructed of a conductive material (e.g., a metal) and, in some instances, an insulator (e.g., a polymer). Multiple wires can be grouped together into a strand or channel.

As used herein, the term "module" can refer to a separable component of a medical device system.

As used herein, the term "patient" can refer to a mammal, such as a human.

II. Overview

An implantable inline high density connector is described herein that provides an increased volume density compared to previously-available inline connectors (while occupying a smaller space than previously-available inline connectors) by eliminating all of the empty space and air pockets within the connector. The implantable in-line high density connector can be used with an implantable medical device system to allow modules to be disconnected/reconnected from/to the implantable medical device system in a surgical or implementation field without affecting the rest of the implantable medical device system.

4

The implantable inline high density connector described herein is volumetrically smaller with a higher density than presently-available inline connectors (like Medtronic's Bal Seal). For example, the density of the implantable in-line high density connector is at least four-times greater than that of Medtronic's Bal Seal. As a result, the implantable inline high density connector can be used in new implantable medical device systems that contain 8, 16, 32, 64, or more channels safely while acceptable levels of overall system volume can be preserved.

III. Systems

FIG. 1 illustrates an implantable inline high density connector 10 that can be part of a medical device system, like a neuromodulation system, a cardiac pacemaker, or the like. The implantable in-line high density connector 10 allows modules to be disconnected from and/or reconnected to the implantable medical device system in a surgical or implementation field without affecting the rest of the implantable medical device system. The implantable inline high density connector 10 can be used in implantable medical device systems that contain 8, 16, 32, 64, or more channels. In other words, the implantable inline high density connector 10 can interconnect 8 channels or more, 16 channels or more, 32 channels or more, 64 channels or more, or an even greater number of channels. Additionally, the implantable high density connector 10 can be safe and have a small form factor, preserving acceptable levels of overall system volume.

Generally, the implantable inline high density connector 10 can include a body 12 (including a first half 42 and a second half 44), an input port (IN) 14, and an output port (OUT) 16. As illustrated, the input port (IN) 14 can be included in the second half 44, while the output port (OUT) 16 can be included in the first half 42. It will be understood that the names and functionalities of the input (IN) 14 and the output (OUT) 16, as well as the first half 42 and the second half 44, may be interchangeable. As an example, the dimensions of the first half 42 and the second half 44 can be less than 10 mm high, less than 15 mm long, and less than 50 mm wide. As another example, the dimensions of the first half 42 and the second half 44 can be less than 5 mm high, less than 9 mm long, and less than 50 mm wide. As a further example, the dimensions of the first half 42 and the second half 44 can be less than 2.5 mm high, less than 6.5 mm long, and less than 50 mm wide.

The input port (IN) 14 can receive a lead 15 carrying information from one or more components of the medical device system (e.g., electrodes, actuators, sensors, etc.). The output port (OUT) 16 can receive a lead 17 carrying the information to a different one or more components of the medical device system (e.g., an electronics module). The information from the one or more components of the medical device system can be carried by lead 15 and transmitted through the body 12 to lead 17, which carries the information to the different one or more components of the medical device system. Each of lead 15 and lead 17 is able to be disconnected from the implantable inline high density connector 10, allowing a component of the medical device system to be removed for maintenance or replacement without affecting/disrupting the rest of the medical device system. An example of the lead 15 or the lead 17 including 32 channels 22 is shown in FIG. 2. It should be understood that internal lead wires can be formed in a similar manner.

Each of the 32 channels 22 can include 7 wires 24 enclosed in an insulative casing. Each of the 7 wires 24 can be individually insulated.

Referring again to FIG. 1, the body 12 can be formed by mating a first half 42 to an identical second half 44, which is turned and flipped 180 degrees relative to the first half 42, and then sealing the body 12. For example, the implantable in-line high density connector 10 is implanted during surgery where the first half 42 and the second half 44 can be connected intra-operatively. In this example, dummy connector halves can be attached to the two ends of the two leads which are to be joined. These temporary assemblies can be tunneled under the skin or through the body to the place where the first half 42 and the second half 44 are planned to be joined. There, the dummy connector halves can be removed and the leads can interconnected through the first half 42 and the second half 44 in that location.

The first half 42 and the second half 44 can have symmetrical designs that allows for interchangeable connection between components of the medical device system. The first half 42 and the second half 44 can each include housing and a silicon insert with printed pads/connections. The body 12 can be sealed by tightening screws 32a (entering from the top of the first half 42) and 32b (entering from the bottom of the second half 44). For example, the screws can be made of titanium or stainless steel. The screws 32a, 32b can be set screws. The body 12 can further eliminate all of the empty space or air pockets within the implantable inline high density connector 10. For example, the first half 42 and the second half 44 can mate in a reversible, clamshell-like design. Since the first half 42 and the second half 44 are identical, the first half 42 and the second half 44 can be manufactured by the same process, simplifying manufacturing. Advantageously, since the first half 42 and the second half 44 are identical and have the same design used for both halves, there are no dissimilar male and female halves of the connector to mate together. The first half 42 and the second half 44 each include conductive paths in a same design, e.g., identical printed pads/connections. After being turned and flipped by 180 degrees, the second half 44 mates with the first half 42 to form electrical and mechanical interconnections. The electrical and mechanical interconnections are fundamentally transverse to the direction of the lead 15 and the lead 17.

Figures 3, 4:
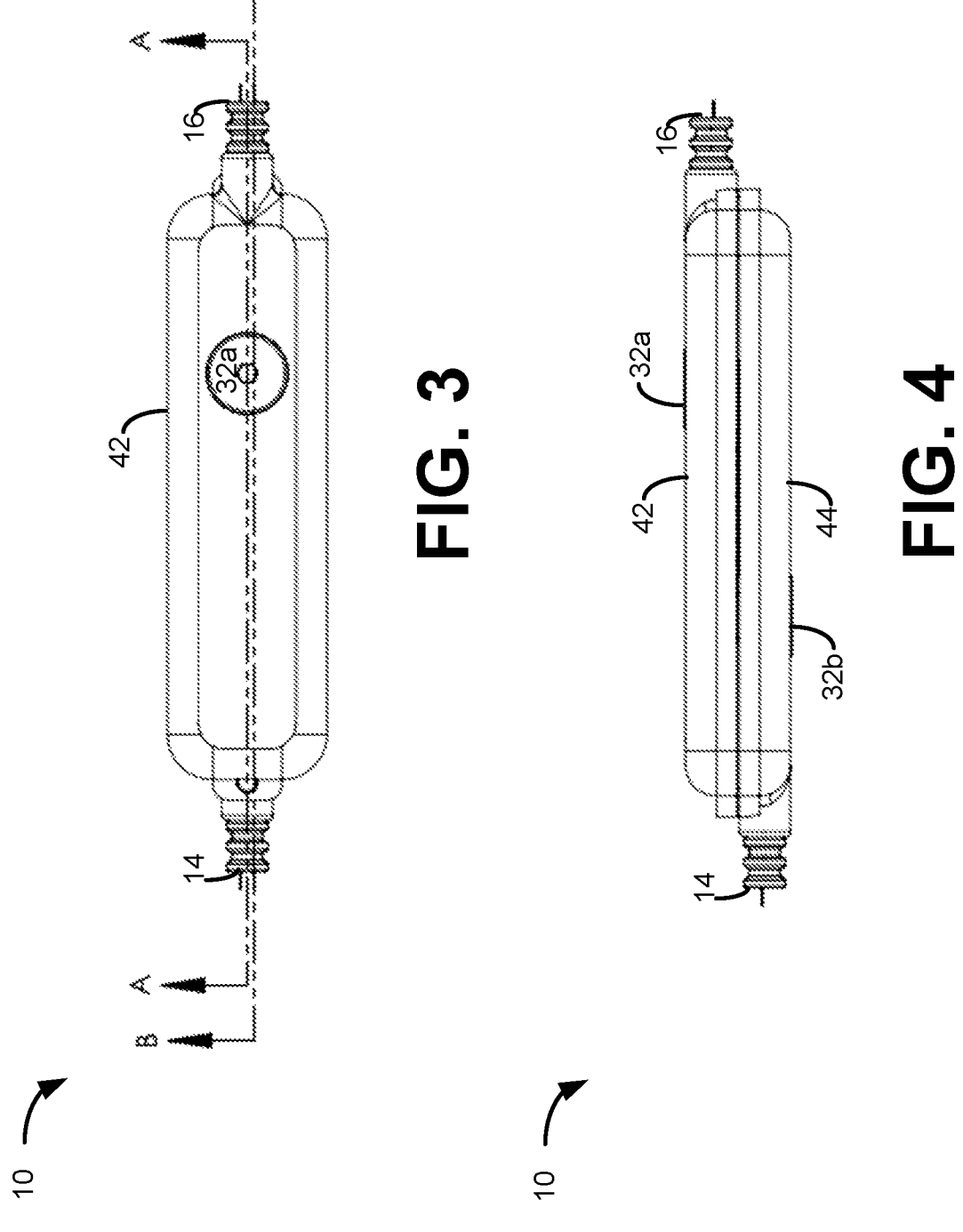
FIG. 3 is a top view of an implantable inline high density connector.
FIG. 4 is a side view of an implantable inline high density connector.

A top view of the outside of implantable inline high density connector 10 (or connector housing of the first half) is shown in FIG. 3. Due to the symmetry of the implantable inline high density connector 10, a bottom view would be similar, just rotated 180 degrees. FIG. 3 shows screw 32a and first half 42 with input port (IN) 14 and output port (OUT) 16. FIG. 4 shows a side view of the outside of implantable inline high density connector 10 (or connector housings of the first half and the second half). The side view shows first half 42 and second half 44, each with their own set screw 32a and 32b, offset by 180 degrees. FIG. 4 also shows the input port (IN) 14 that is part of the second half 44 and the output port (OUT) 16 that is part of the first half 42. The first half 42 and the second half 44 can be sealed together by tightening screws 32a and 32b. The seal created by tightening the screws 32a, 32b can retard moisture ingress into the implantable inline high density connector 10.

Figure 5:
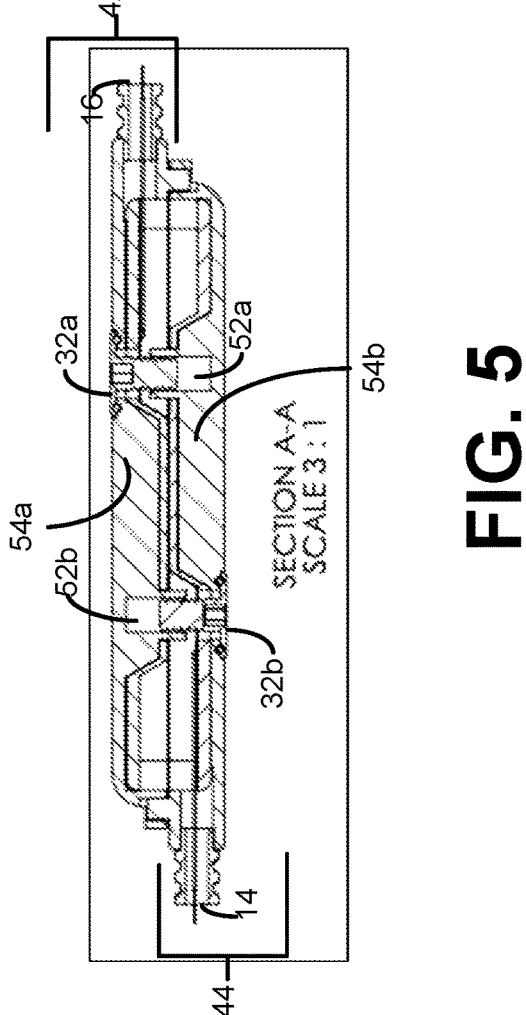
FIG. 5 is a cut view of section A-A of FIG. 3.

FIG. 5 shows a cut view of the inside of the implantable inline high density connector 10 at the line A-A of FIG. 3 (at a 3:1 scale). The input port (IN) 14 that is part of the second half 44 and the output port (OUT) 16 that is part of the first half 42 are both shown. The first half 42 and the second half

Figure 6:
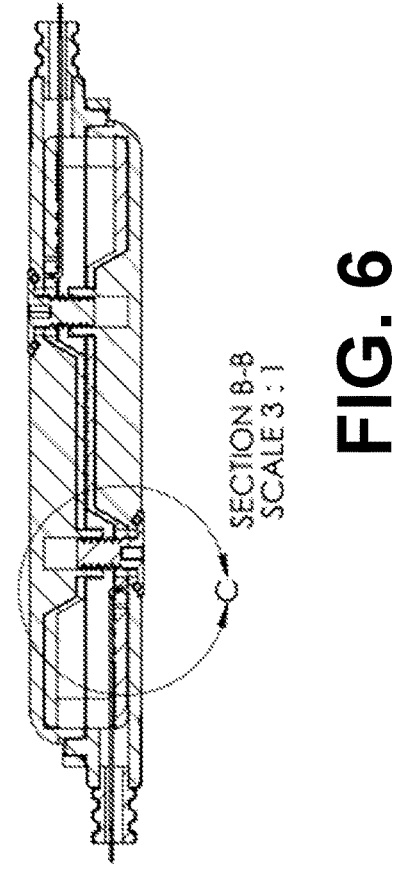
FIG. 6 is a cut view of section B-B of FIG. 3.
Figure 7:
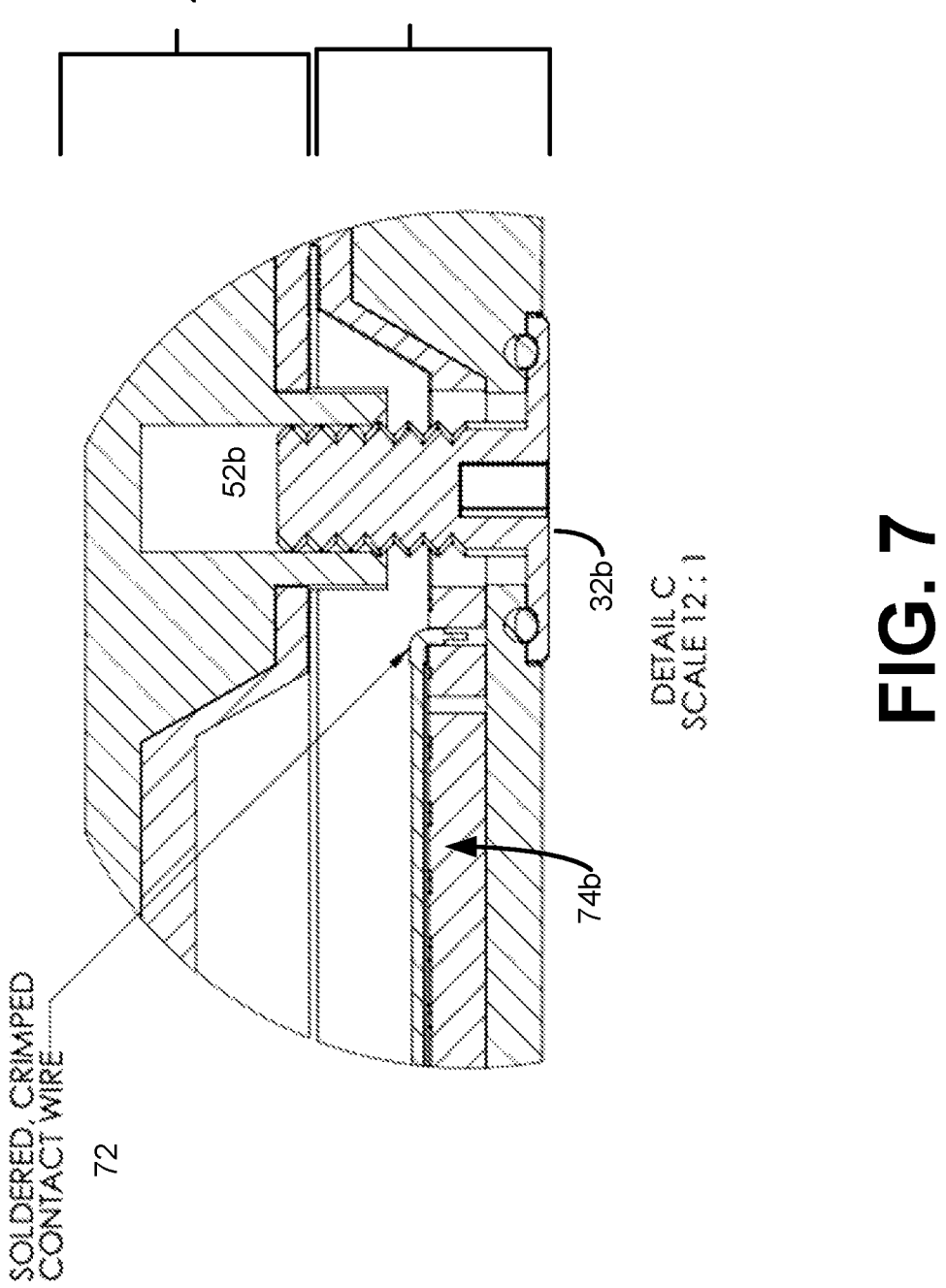
FIG. 7 is cut view of detail C of FIG. 3.

44 extend horizontally from the respective port to the end of the device; it should be clear that the first half 42 and the second half 44 are identical and rotated by 180 degrees. Each of the first half 42 and the second half 44 includes a raised deformable mating surface 54a, 54b to ensure electrical contact between conductor pairs on the mating surfaces. In some instances, areas other than the mating area can be filled with a material (e.g., an insulating material like silicone). The set screws 32a, 32b are shown as traversing the first half 42 and the second half 44 and leaving an empty (or filled) area in screw holes 52b, 54b. FIG. 6 is identical to FIG. 5, showing a cut view of the inside of the implantable inline high density connector 10 at line B-B of FIG. 3, and shows the location of detail C, which is shown in FIG. 7. Detail C, in FIG. 7, shows a zoomed in view of a portion of the inside of implantable inline high density connector 10 at a 12:1 scale. In the area between the first half 42 and the second half 44 detail C shows a soldered, crimped contact wire (one wire lead 72) and a portion of printed pads 74b. The printed pads 74b have conductive connection points (e.g., holes in their center) to connect to the wire lead 72 with the conductive pathways of the implantable inline high density connector 10. It should be understood that the conductive pathways formed can be conductive polymer links or printed/etched metal links.

Figure 8:
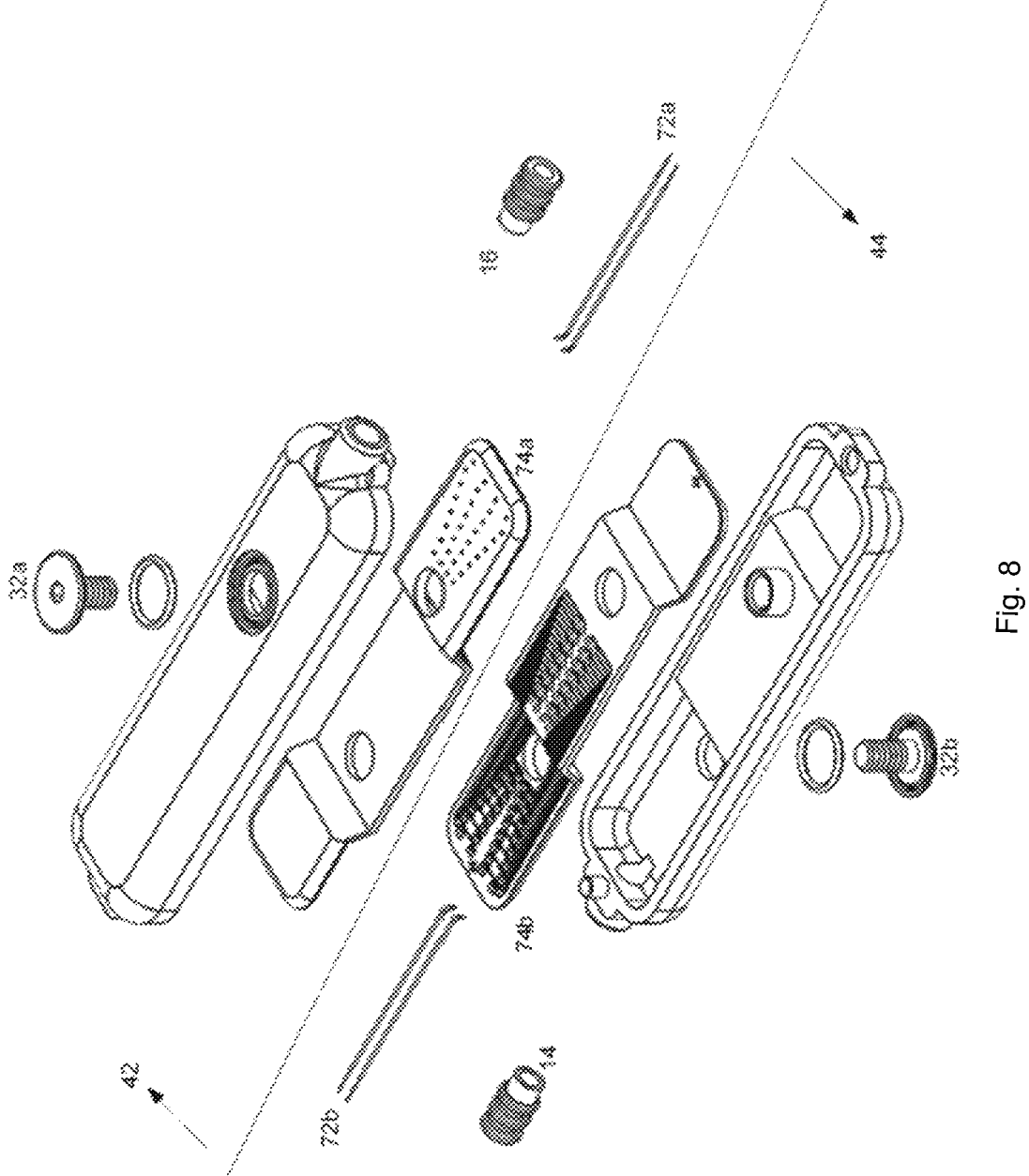
FIG. 8 is an exploded view of an implantable inline high density connector device.

FIG. 8 is an exploded view of the implantable inline high density connector 10. The first half 42 and the second half 44 include the same parts, flipped and rotated 180 degrees. Each half 42, 44 includes a port (input port (IN) 14 or output port (OUT) 16), wire leads 72a, 72b that each enter through a port, an insert (e.g., silicon insert) with printed conducting pads/pathways 74a, 74b, screws 32a, 32b, and enclosures. The enclosures can be made of a plastic and/or a metal material. For example, the enclosures can include titanium and/or PEEK plastic. The printed conducting pads/pathways 74a, 74b are designed to ensure reliable contact between connector pairs, provide a high connector conductor density, make electrical and mechanical interconnections that are transverse to the direction of the incoming or outgoing lead wires, connect/reconnect in a specific deployed field, and/or employ printed conductive substrates. In some instances, the implantable inline high density connector 10 can have one or more internal capsules filled with one or more hydrophobic materials (e.g., PDMS) to retard moisture ingress and to avoid an internal void or an air cavity within the implantable inline high density connector. In other instances, each half 42, 44 can be filled with a material (e.g., a hydrophobic material like silicone) that is allowed to cure before mating (leaving only the mating surface open so that the mating surfaces touch each other.

Figure 9:
FIG. 9 is the bottom half of the implantable inline connector of FIG. 8 assembled.
Figure 10:
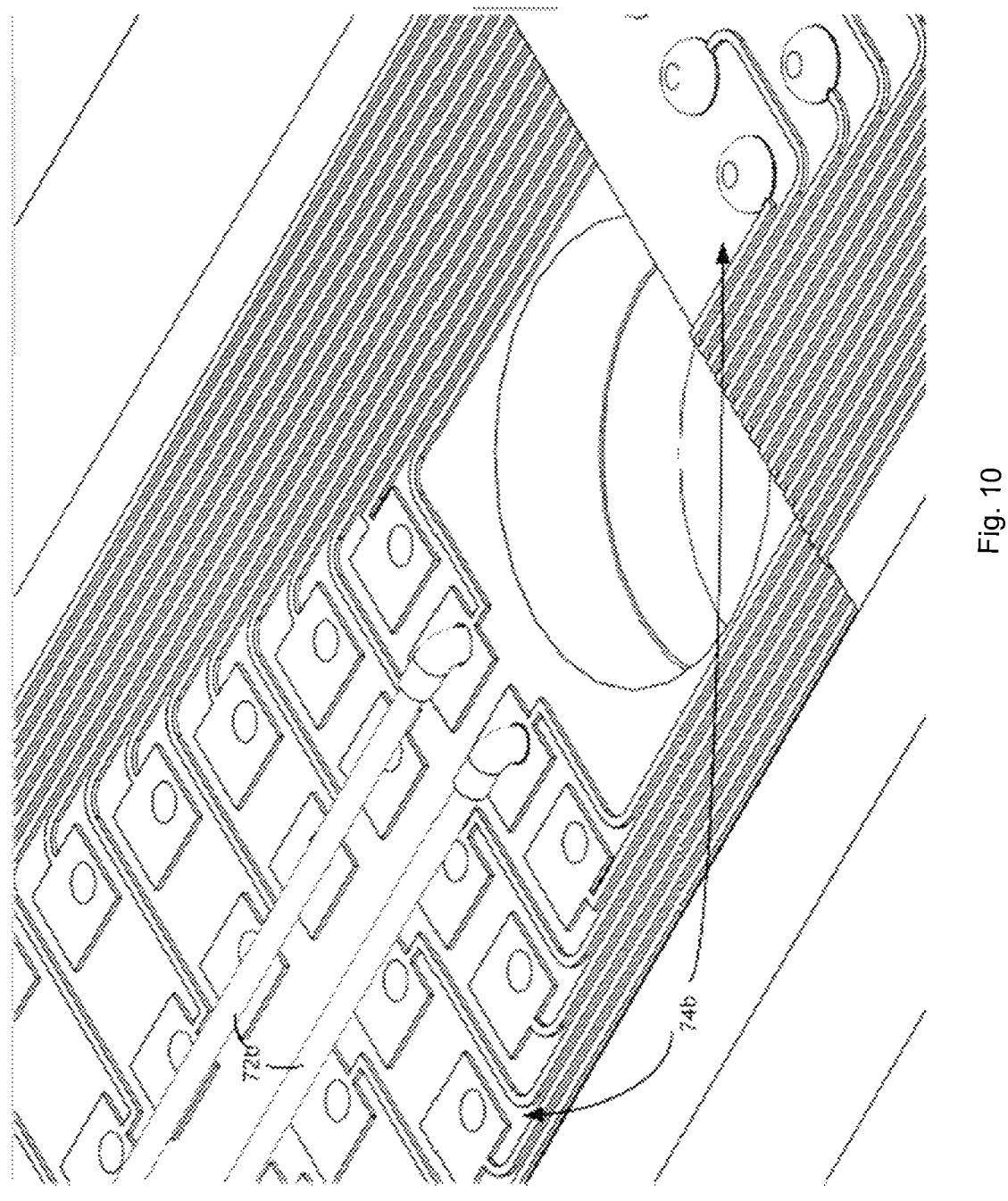
FIG. 10 is a zoomed in illustration of the bottom half of the implantable inline connector of FIG. 9.

FIG. 9 shows the interior of the second half 44 (shown as the bottom half) of the body 12. The top half (or the first half 42) of the body 12 is identical to FIG. 9 when FIG. 9 is flipped and rotated by 180 degrees in the longitudinal direction. FIG. 10 shows a zoomed in portion of FIG. 9, with the conductive pads/pathways 74b and the wire leads 72b shown in greater detail. Each of half of the implantable inline high density connector can include two sets (or arrays) of conductive pads, first and second sets of conductive pads, that are connected by conductive pathways. One conductive pathway can attach a first conductive pad with a second conductive pad. Each wire lead 72b can be electrically connected to a first conductive pad of the first set of conductive pads. The second set of conductive pads can be on the raised mating surface of the second half 44 of implantable inline high density connector 10. The same is true for the first half 42 (not shown). When the first half 42 and the second half 44 are sealed together the second set of conductive pads on each mating surface (also called the conductor pairs) can be in electrical and/or mechanical connection to allow signals to travel from lead wires 72_b_ through the conductive pads and pathways to lead wires 72_a_. In this way the channels and wires associated with different components of medical device systems can be interconnected inside the implantable inline high density connector 10.

The implantable inline high density connector 10 can be manufactured using one or more manufacturing technologies. For example, the fabrication of the components of the implantable inline high density connector 10 can be facilitated by the use of an aerosol printing technology (e.g., Nano Jet) to make conducting pads and pathways within the implantable inline high density connector 10. The conductive pads, and optionally the entire implantable inline high density connector 10, can be made of a bio-compatible material. Electrical joints can be created at the conductive pads by attaching at least a portion of the wire leads 72_b_ to the conductive pads by at least one of laser welding, soldering, conductive epoxy, etc. The conductive pads and pathways can be formed of conductive polymers or metals. The conductive pads and pathways can condition, act upon, distribute, etc., signals between the connected components of the medical device system. The pathways can be formed by focused aerosol printing, masked physical vapor deposition, electroplating, etching of bulk conductive materials, or the like. Each incoming wire lead 72_b_ entering through the input port (IN) 14 can be electrically attached to a printed conductive pad on second half 44. Not shown, each wire lead 72_a_ entering through the output port (OUT) 16 can be electrically attached to a printed conductive pad on first half 42. There are two possible configurations of the printed metal pattern on the silicone inserts of implantable inline high density connector 10, as shown in the exploded view of FIG. 8, one for facilitating subsequent electroplating of metal and the other that does not accommodate electroplating. Additionally, the edges of the raised bumps in the molded silicone inserts may need to be chamfered or rounded in such a way that the incoming stream of ink particles during the printing process does not have to traverse a 90 degree bend in the silicone shape. By rounding the edges in this way, the continuity of the electrical current path is better assured.

IV. Methods

Figure 11:
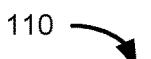
FIG. 11 is a process flow diagram of a method for using the implantable inline high density connector device to allow a module to be disconnected without affecting the entire implanted medical device system.
Figure 12:
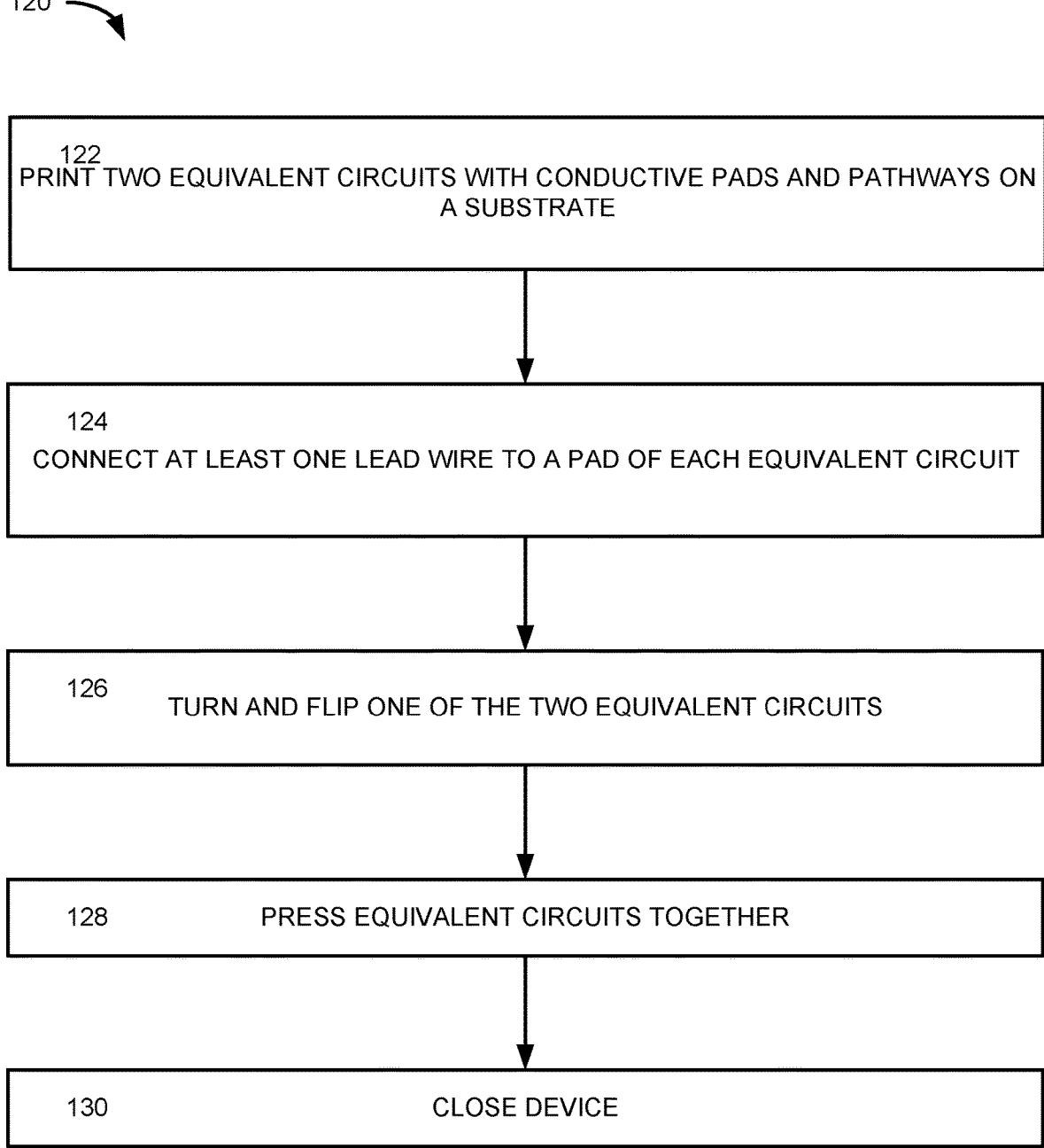
FIG. 12 is a process flow diagram of a method for constructing the implantable inline high density connector device.

In view of the foregoing structural and functional features described above, methods 110 of FIGS. 11 and 120 of FIG. 12 are described. While, for the purposes of simplicity of explanation, the example methods of FIGS. 11 and 12 are shown and described as executing serially, the present examples are not limited by the illustrated order, as some actions could in other examples occur in different orders or concurrently from that shown and described herein. Moreover, it is not necessary that all described actions be performed to implement the methods 110 and 120.

Referring now to FIG. 11, method 110 can be performed when inline connector 12 is implanted as part of a medical device system. At 112 a medical device system can be implanted in a patient's body with an inline implantable connector (e.g., inline connector 12). The medical device system can be, for example, a neuromodulation system, a cardiac pacemaker, or the like, and can include electrodes, actuators, sensors, etc. and an electronics module. The inline implantable connector separates the electronics module and the electrodes, actuators, sensors, etc. The implantable inline high density connector is described herein provides an increased volume density (while occupying a smaller space than previously-available inline connectors) by eliminating all of the empty space and air pockets within the connector.

At 114, a need to maintain or replace the electronic module in the medical device system can be detected. For example, the need for maintenance or replacement may be due to an age of the medical device system or a change in behavior of the electronics module. At 116, the electronic module can be disconnected from the inline implantable connector to maintain or replace the electronic module. The electronics module can be removed from the system in a modular fashion (without affecting the other components of the system). The repaired electronic module, or a new electronic module, can then be re-connected to the inline implantable connector without disrupting the other components of the medical device system. Therefore, the inline implantable connector device makes the implantable medical device system as a whole more reparable and safer.

As shown in FIG. 12, method 120 illustrates a method for constructing an implantable inline high-density connector. For example, the components of FIG. 8 can be assembled to form the implantable inline high density connector. It should be understood that the following steps can occur in a different order than laid out here. Additionally, more steps may be required than those illustrated.

At 122, two equivalent circuits can be printed on a substrate. The substrate can be a silicone insert, but other substrate materials are contemplated. The circuits printed on the substrate can include conductive pads and pathways. Additionally, the substrates can be bent, molded, or formed in a non-flat manner, to create raised mating surfaces that facilitate contact at a mating area between the two halves of the implantable inline high density connector. At 124 at least one lead wire can be connected to pads on the proximal end of a metal trace that terminates at the conductive mating pad on the distal end, forming a complete circuit when the connector halves are mated. It should be noted that more than one lead wire may be connected within the circuit.

The substrates can be placed within a housing (either before or after the wires are connected). After leads are attached, the housing can be filled with a material (e.g., one or more hydrophobic materials, such as silicone) that is then allowed to cure so that only the mating surface extends above the level of the rim of the connector half. It should be noted that all of the empty space and air pockets within the connector are removed and can be removed in other ways than filling with a material. For example, the implantable inline high-density connector can have an internal capsule filled with one or more hydrophobic materials to retard moisture ingress. At 126, one of the two equivalent circuits can be turned and flipped 180 degrees. At 128, the equivalent circuits can be pressed together to establish a conductive path (e.g., the conductive pads on the mating surfaces are in electrical and/or mechanical connection). At 130, the device can be closed/sealed, for example by tightening screws inserted through holes extending at least partially though each side of the housing. The mating surfaces can also be self-sealing to retard moisture ingress.

From the above description, those skilled in the art will perceive improvements, changes and modifications. Such improvements, changes and modifications are within the skill of one in the art and are intended to be covered by the appended claims.

The following is claimed:

1. An inline implantable connector device used in medical device systems and occupying a limited volume, the inline implantable connector device comprising:

a first half and a second half each comprising a conductive path in a same design, wherein the first half and the second half are identical and are interchangeably connectable with components of the medical device systems within a surgical implementation field without affecting a remainder of the medical device systems, wherein the second half is turned and flipped by 180 degrees to mate with the first half so that the conductive paths interconnect to form electrical and mechanical interconnections that are fundamentally transverse to the direction of incoming or outgoing lead bodies;

a first screw hole on a top side of the connector device to accept a screw therethrough; and a second screw hole on a bottom side of the connector device to accept another screw therethrough.

2. The inline implantable connector device of claim 1, wherein the first half and the second half are sealed together by tightening the screw and the other screw.

3. The inline implantable connector device of claim 2, wherein the first half and the second half are sealed together to retard moisture ingress into the inline implantable connector device.

4. The inline implantable connector device of claim 1, further comprising at least one port on the first half for incoming wires to enter and at least one port on the second half for outgoing wires to exit.

5. The inline implantable connector device of claim 4, wherein the incoming or outgoing wires terminate at biocompatible conductive pads.

6. The inline implantable connector device of claim 5, wherein electrical joints are created at the bio-compatible conductive pads when the incoming or outgoing wires terminate and the electrical joints are formed by laser welding, soldering, or conductive epoxy.

7. The inline implantable connector device of claim 6, wherein the first half and the second half each comprise a high density of bio-compatible conductive pads.

8. The inline implantable connector device of claim 5, wherein the bio-compatible conductive pads make electrical and mechanical interconnections that are transverse to the direction of the incoming or outgoing wires.

9. The inline implantable connector device of claim 1, wherein the conductive pads are flexible to ensure reliable contact between connector pairs, including a conductive pad of the first half and a conductive pad of the second half, when the first half and the second half are mated.

10. The inline implantable connector device of claim 1, wherein the first half and the second half are each less than 10 mm high, less than 15 mm long, and less than 50 mm wide.

11. The inline implantable connector device of claim 1, wherein the first half and the second half are each less than 5 mm high, less than 9 mm long, and less than 50 mm wide.

12. The inline implantable connector device of claim 1, wherein the first half and the second half are each less than 2.5 mm high, less than 6.5 mm long, and less than 32 mm wide.

13. The inline implantable connector device of claim 1, wherein the inline implantable connector device is configured for multiple disconnections and reconnections in a surgical or implementation field.

14. The inline implantable connector device of claim 1, wherein the first half and the second half provide a symmetrical design that allows for interchangeable connection between multiple high density systems whose components are interconnected using lead bodies.

15. The inline implantable connector device of claim 1, wherein the conductive paths comprise an array of conductive polymers or metals, the array is configured to condition, act upon, and/or distribute signals between connected systems.

16. The inline implantable connector device of claim 15, wherein the array of internal conductive paths is formed by focused aerosol printing, masked physical vapor deposition, electroplating, or laser etching of bulk conductive materials.

17. The inline implantable connector device of claim 1, further comprising an internal capsule filled with one or more hydrophobic materials to retard moisture ingress.

18. The inline implantable connector device of claim 17, wherein one or more hydrophobic materials comprise polydimethylsiloxane (PDMS).

19. The inline implantable connector device of claim 1, wherein the conductive paths comprise conductive polymer links or printed/etched metal links.

20. The inline implantable connector device of claim 1, wherein the first half and the second half comprise raised, deformable mating surfaces to ensure electrical contact between conductor pairs.

21. The inline implantable connector device of claim 20, wherein the mating surfaces are continuous and self-sealing to retard water ingress.

* * * * *